US007863273B2

(12) United States Patent
Pillai et al.

(10) Patent No.: US 7,863,273 B2
(45) Date of Patent: Jan. 4, 2011

(54) PROCESS FOR THE PREPARATION OF AN OPTICALLY ACTIVE 5H-PYRROLO [3,4-B] PYRAZINE DERIVATIVE

(75) Inventors: Biju Kumar Gopinathen Pillai, Navi Mumbai (IN); Sankar Arjunan, Navi Mumbai (IN); Nitin Sharad Chandra Pradhan, Thane (IN); Narendra Shriram Joshi, Navi Mumbai (IN)

(73) Assignee: Glenmark Generics Ltd., Mumbai (IN)

( * ) Notice: Subject to any disclaimer, the term of this patent is extended or adjusted under 35 U.S.C. 154(b) by 0 days.

(21) Appl. No.: 12/087,829

(22) PCT Filed: Dec. 29, 2006

(86) PCT No.: PCT/IB2006/003801

§ 371 (c)(1),
(2), (4) Date: Oct. 27, 2008

(87) PCT Pub. No.: WO2007/083188

PCT Pub. Date: Jul. 26, 2007

(65) Prior Publication Data

US 2009/0054441 A1  Feb. 26, 2009

(30) Foreign Application Priority Data

Jan. 17, 2006 (IN) .......................... 76/MUM/2006
May 4, 2006 (IN) ......................... 699/MUM/2006

(51) Int. Cl.
*A61K 31/525* (2006.01)

(52) U.S. Cl. ....................... 514/249; 544/350; 544/360; 546/268.1

(58) Field of Classification Search ................. 514/249; 544/350, 360; 546/268.1
See application file for complete search history.

(56) References Cited

U.S. PATENT DOCUMENTS

| 3,580,923 | A | 5/1971 | Leigh |
| 6,436,936 | B1 | 8/2002 | Young et al. |
| 6,444,673 | B1 | 9/2002 | Cotrel et al. |
| 6,969,767 | B1 | 11/2005 | Bayod et al. |

FOREIGN PATENT DOCUMENTS

| EP | 1 457 487 | 9/2004 |
| WO | WO 93/16035 | 8/1993 |
| WO | WO 2005/047274 | 5/2005 |
| WO | WO 2005/097132 | 10/2005 |

OTHER PUBLICATIONS

Yaping et al., "Synthesis of enantiomerically pure desmethylzopiclone and determination of its absolute configuration", *Tetrahedron: Asymmetry*, vol. 11, 2000, pp. 4623-4627.
Wilen et al., "Tetrahedron report No. 38: Strategies in optical resolutions", *Tetrahedron, Elsevier Science Publishers*, vol. 33, No. 21, 1977, pp. 2725-2736.

*Primary Examiner*—James O Wilson
*Assistant Examiner*—Douglas M Willis
(74) *Attorney, Agent, or Firm*—M. Carmen & Associates, PLLC

(57) ABSTRACT

A substantially pure dextrorotatory isomer of zopiclone or a pharmaceutically acceptable salt thereof and crystalline forms thereof are provided. Also provided is a process for its preparation and pharmaceutical compositions containing same.

8 Claims, 2 Drawing Sheets

PROCESS FOR THE PREPARATION OF AN OPTICALLY ACTIVE 5H-PYRROLO [3,4-B] PYRAZINE DERIVATIVE

CROSS-REFERENCE TO RELATED APPLICATION

This application claims priority under 35 U.S.C. §371 to International Application No. PCT/IB2006/003801, filed Dec. 29, 2006 and entitled "IMPROVED PROCESS FOR THE PREPARATION OF AN OPTICALLY ACTIVE 5H-PYRROLO[3,4-B]PYRAZINE DERIVATIVE", which claims priority to Indian Provisional Application No. 76/MUM/2006, filed on Jan. 17, 2006, and entitled "PROCESS FOR THE PREPARATION OF AN OPTICALLY ACTIVE 5H-PYRROLO[3,4-B]PYRAZINE DERIVATIVES" and to Indian Provisional Application No. 699/MUM/2006, filed on May 4, 2006, and entitled "PROCESS FOR THE PREPARATION OF ESZOPICLONE", the contents of each of which are incorporated by reference herein.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL

Not Applicable

BACKGROUND OF THE INVENTION

1. Field of the Invention

The present invention generally relates to an improved process for the separation of a mixture of enantiomers of 5H-pyrrolo[3,4-b]pyrazine derivatives. More specifically, the present invention relates to a process for the preparation of dextrorotatory isomer of zopiclone by resolution of zopiclone by means of an optically active acid, in an appropriate organic solvent. The present invention also relates to a process for resolution of eszopiclone and salts thereof. The present invention further relates to a crystalline form of eszopiclone and process for its preparation.

2. Description of the Related Art

Eszopiclone, also known as the dextrorotary isomer of zopiclone or (+)-(5S)-6-(chloropyridin-2-yl)-7-oxo-6,7-dihydro-5H-pyrrol[3,4-b]pyrazin-5-yl 4-methylpiperazine-1-carboxylate) is represented by the structure of Formula I.

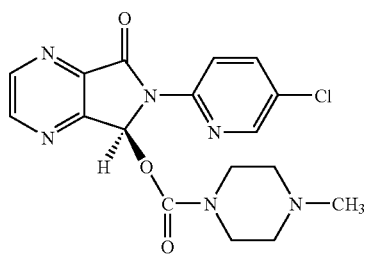

(I)

Eszopiclone is a nonbenzodiazepine hypnotic agent that is a pyrrolopyrazine derivative of the cyclopyrrololone class. Eszopiclone is indicated for the treatment of insomnia. Eszopiclone is commercially sold under the trade name Lunesta®. See, e.g., Physician's Desk Reference, "Lunesta" 60th Edition, p. 3139-3143 (2005).

French Patent No. 72.00505 (published under number 2.166.314) discloses zopiclone (also known as 6-(5-chloropyrid-2-yl)-5-(4-methylpiperazin-1-yl)carbonyloxy-7-oxo-6,7-dihydro-5H-pyrrolo[3,4-b]pyrazine), which may act as a hypnotic product. Due to the presence of an asymmetric carbon atom at the 5-position of the 5H-pyrrolo[3,4-b]-pyrazine ring-system, zopiclone is considered to be in racemic form, that is, consisting of an equimolecular mixture of the laevorotatory and dextrorotatory forms.

It is known that in a racemic mixture, one of the two enantiomers is often more active than the other and that an enhancement of the toxicity may be linked to this activity. The other enantiomer is generally less active or even inactive and less toxic. For such products, the gain in activity does not compensate for the drawbacks due to the enhanced toxicity. In the case of zopiclone, it was found that not only was the dextrorotatory isomer approximately twice as active with lower toxicity as compared to the racemate, but that the laevorotatory isomer is both almost inactive and more toxic than the racemate.

U.S. Pat. No. 6,444,673 discloses processes for the preparation of the dextrorotatory isomer of zopiclone by resolving zopiclone with D(+)-O,O'-dibenzoyltartaric acid as an optically active acid in one or more organic solvents chosen from halogenated aliphatic hydrocarbons such as dichloromethane and nitriles such as acetonitrile.

Mixtures of enantiomers are obtained, for instance, in reactions that do not, or only to a small extent, proceed stereoselectively or in reactions in which there is no complete inversion or retention. The physical properties of enantiomers, such as boiling point, melting point and the like, are the same, so that a mixture of enantiomers cannot be separated using the customary separation techniques. In one of the methods for the separation of mixtures of enantiomers, an optically active resolving agent is used to convert both enantiomers into the corresponding diastereomers. As the physical properties of these diastereomers do differ, the diastereomers can, at any rate in principle, subsequently be separated by, for instance, crystallization or chromatography, both diastereomers being obtained in substantially chemically pure and optically enriched form. The diastereomer can in a third step again be separated into the corresponding, optically enriched enantiomer and the optically active resolving agent. Several processes and optically active resolving agents for the separation of enantiomers are, for example, extensively described in "Stereochemistry of Organic Compounds" by E. L. Eliel and S. H. Wilen (Wiley Interscience), 1994).

As a result of the presence of an asymmetric carbon atom at the 5-position of the 5H-pyrrolo[3,4-b]-pyrazine ring-system, zopiclone must be considered, in racemic form, to consist of a strictly equimolecular mixture of the laevorotatory and dextrorotatory forms.

From the standpoint of the potency of action in the main tests demonstrating the tranquilizing and hypnotic activity of zopiclone, such as the test of affinity for central benzodiazepine receptor sites according to the technique of J. C. Blanchard and L. Julou, J. of Neurochemistry, 40, 601 (1983) based on the work of Squires and Braestrup, Nature, 266, 732-734 (1977), or the test of antagonist activity with respect to pentetrazol-induced convulsions according to the technique of Everett and Richards, J. Pharmacol., 81, 402 (1944), or in the writhing reflex test in mice according to the technique of Zbinden and Randall, Advances in Pharmacology 5, 213-291 (1967), the dextrorotatory isomer is approximately twice as active whereas the laevorotatory isomer is almost inactive.

It is common knowledge that finding the right resolving agent for the separation of mixtures of enantiomers by crystallization of a mixture of diastereomers is in practice a laborious and highly time-consuming process, for a correct choice of the resolving agent cannot in advance be made, not even when applying advanced techniques such as, for example, computer simulations or X-ray diffraction, and thus has to be found by trial and error for each mixture of enantiomers anew. This implies that for the separation of enantiomers via diastereomers often many experiments have to be conducted, while the individual experiments may take a long time on account of tedious crystallization. It will therefore be clear that the search for a good resolving agent for the separation of mixtures of enantiomers of a compound and the conditions under which good results are obtained is a time-consuming matter and the chance of success is unpredictable. Accordingly, there remains a need for an improved process for the resolution of eszopiclone that eliminates and reduces the problems of the prior art on a commercial scale in a convenient and cost efficient manner.

BRIEF SUMMARY OF THE INVENTION

In accordance with one embodiment of the present invention, a substantially pure dextrorotatory isomer of zopiclone or a pharmaceutically acceptable salt thereof is provided.

In accordance with a second embodiment of the present invention, a pharmaceutical composition is provided comprising a therapeutically effective amount of a substantially pure dextrorotatory isomer of zopiclone or a pharmaceutically acceptable salt thereof.

In accordance with a third embodiment of the present invention, a crystalline di-p-toluyl-D tartarate salt of zopiclone is provided.

In accordance with a fourth embodiment of the present invention, a pharmaceutical composition is provided comprising a therapeutically effective amount of a crystalline di-p-toluyl-D tartarate salt of zopiclone.

In accordance with a fifth embodiment of the present invention, a crystalline dextrorotatory isomer of zopiclone is provided.

In accordance with a sixth embodiment of the present invention, a pharmaceutical composition is provided comprising a therapeutically effective amount of a crystalline dextrorotatory isomer of zopiclone.

In accordance with a seventh embodiment of the present invention, a process for the preparation of a dextrorotatory isomer of zopiclone is provided comprising:
  (a) providing a reaction mixture comprising zopiclone in one or more first solvents and one or more optically active acids;
  (b) crystallizing the desired isomer by substantially removing the first solvent and adding one or more second solvents;
  (c) recrystallizing a salt using a solvent selected from the group consisting of an ether-containing solvent, alcohol-containing solvent, ketone-containing solvent and mixtures thereof;
  (d) alkalizing the recrystallized salt with an inorganic base in water or a solvent mixture comprising water and a halogenated solvent to obtain the dextroisomer; and
  (e) isolating the resulting dextroisomer isomer of zopiclone.

In accordance with an eighth embodiment of the present invention, a process for the preparation of a dextrorotatory isomer of 6-(5-chloro-2-pyridyl)-5-[(4-methyl-1-piperazinyl)-carbonyloxy]-7-oxo-6,7-dihydro-5H-pyrrolo[3,4-b]pyrazine or a pharmaceutically acceptable salts thereof by resolving 6-(5-chloro-2-pyridyl)-5-[(4-methyl-1-piperazinyl)-carbonyloxy]-7-oxo-6,7-dihydro-5H-pyrrolo[3,4-b]pyrazine using an optically active acid selected from the group consisting of D-lactic acid, D-tartaric acid, D-malic acid, 1S-10-camphor sulfonic acid, S-hydratropic acid, (S)-2-methoxy phenyl acetic acid, (R)-2-methoxy-2-trifluoromethyl phenylacetic acid, D-mandelic acid, Di-p-anisoyl-D-tartaric acid, D-tartaric acid momoparachloro anilide, Dibenzoyl-D-tartaric acid monodimethyl amide, S(+)-1,1'-binaphthalene-2,2'-dihydrogen phosphate, Di-p-toluyl-D-tartaric acid and in an appropriate organic solvent.

DEFINITIONS

The term "treating" or "treatment" of a state, disorder or condition as used herein means: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statistically significant or at least perceptible to the patient or to the physician.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host causing a therapeutically effective blood concentration of the active ingredient at the particular location. This can be accomplished, e.g., by topical, local or by systemic administration of the active ingredient to the host.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dehydrate and other such material known to those of ordinary skill in the art.

The term "sweetening agent" as used herein is intended to mean a compound used to impart sweetness to a formulation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in granulations. Such compounds include, by way of example and without limitation, acacia alginic acid, tragacanth, carboxymethylcellulose sodium, poly (vinylpyrrolidone), compressible sugar (e.g., NuTab), ethylcellulose, gelatin, liquid glucose, methylcellulose, povidone and pregelatinized starch, combinations thereof and other material known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC™ F68, PLURONIC™ F127), collagen, albumin, celluloses in nonaqueous solvents, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art.

The term "diluent" or "filler" as used herein is intended to mean inert substances used as fillers to create the desired bulk, flow properties, and compression characteristics in the preparation of solid dosage formulations. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in solid dosage formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in solid dosage formulations to reduce friction during compression of the solid dosage. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage formulations to promote the disruption of the solid mass into smaller particles which are more readily dispersed or dissolved. Exemplary disintegrants include, by way of example and without limitation, starches such as corn starch, potato starch, pre-gelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthalate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type, also known as superinone or triton) is another useful wetting agent, combinations thereof and other such materials known to those of ordinary skill in the art.

Most of these excipients are described in detail in, e.g., Howard C. Ansel et al., Pharmaceutical Dosage Forms and Drug Delivery Systems, (7th Ed. 1999); Alfonso R. Gennaro et al., Remington: The Science and Practice of Pharmacy, (20th Ed. 2000); and A. Kibbe, Handbook of Pharmaceutical Excipients, (3rd Ed. 2000), which are incorporated by reference herein.

BRIEF DESCRIPTION OF THE SEVERAL VIEWS OF THE DRAWING(S)

DETAILED DESCRIPTION OF THE INVENTION

One embodiment of the present invention provides a process for obtaining a dextrorotatory isomer of zopiclone or a pharmaceutically acceptable salt thereof. In one embodiment, the process includes at least resolving zopiclone (i.e., 6-(5-chloro-2-pyridyl)-5-[(4-methyl-1-piperazinyl)-carbonyloxy]-7-oxo-6,7-dihydro-5H-pyrrolo[3,4-b]pyrazine) or a pharmaceutically acceptable salt thereof in the presence of an optically active acid, and in a suitable organic solvent.

Zopiclone can be obtained by processes known in the art. Suitable optically active acids for use herein include, but are not limited to, D-lactic acid, D-tartaric acid, D-malic acid, 1S-10-camphor sulfonic acid, S-hydratropic acid, (S)-2-methoxy phenyl acetic acid, (R)-2-methoxy-2-trifluoromethyl phenylacetic acid, D-mandelic acid, di-p-anisoyl-D-tartaric acid, D-tartaric acid momoparachloro anilide, dibenzoyl-D-tartaric acid monodimethyl amide, S(+)-1,1'-binaphthalene-2,2'-dihydrogen phosphate, Di-p-toluyl-D-tartaric acid and mixtures thereof. Preferably, Di-p-toluyl-D tartaric acid is the optically active acid for use herein. The optically active acid may be present in any amount sufficient to form the optically active acid salt of zopiclone, e.g., a di-p-toluyl-D tartarate salt.

Useful solvents include ether-containing solvents, alcohol-containing solvents, ketone-containing solvents and mixtures thereof. Suitable ether-containing solvents include cyclic ethers such as, for example, tetrahydrofuran, 4-dimethyl-tetrahydrofuran, oxetane, methyl-oxetane, dimethyl-oxetane, 3-methyl-tetrahydrofuran, 3-ethyl-tetrahydrofuran, oxepane, oxocane, oxonane, oxecane, perfluoroalkyl oxirane and the like and mixtures thereof, aliphatic ether such as isopropyl ether, methyl t-butyl ether, and the like and mixtures thereof. Preferably, the cyclic ether is tetrahydrofuran. Suitable alcohol-containing solvents include aromatic and aliphatic $C_1$-$C_{12}$ alcohols and the like and mixtures thereof. Suitable aliphatic alcohols include $C_1$-$C_8$ alcohols such as, for example, methanol, ethanol, n-propanol, isopropanol, n-butanol, isobutanol, tert-butanol and the like and mixtures thereof. Suitable aromatic alcohols include $C_3$-$C_{12}$ alcohols such as, for example, benzyl alcohol, benzyloxyethanol, phenoxyethanol and the like and mixtures thereof. Preferably, the alcohol-containing solvent is an aliphatic alcohol with methyl alcohol being most preferred. Suitable ketone-containing solvents include acetone and the like and mixtures thereof.

Figure 1:
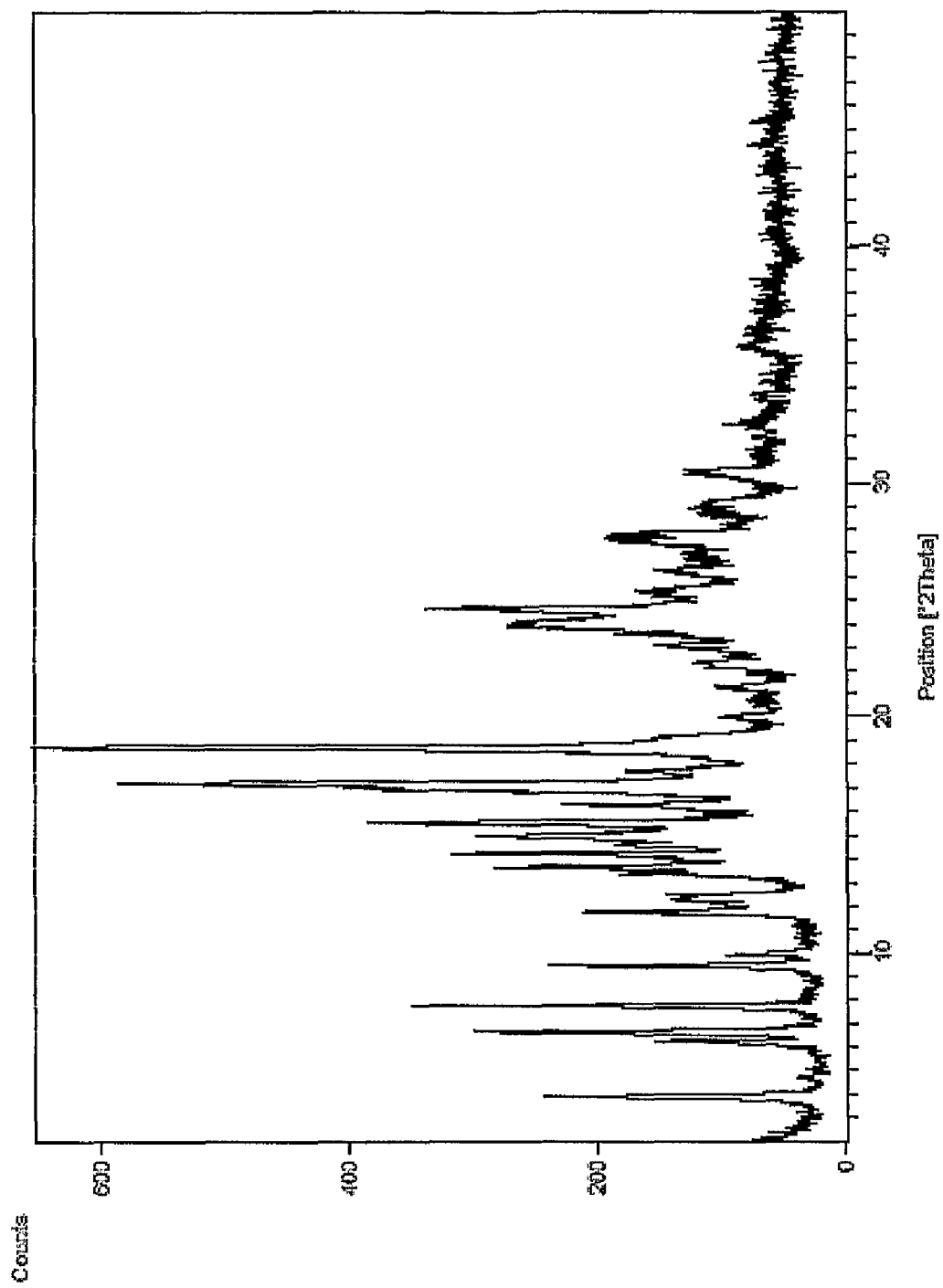
FIG. 1 is a characteristic X-ray powder diffraction pattern of a Di-p-toluyl-D tartarate salt of zopiclone in crystalline form.

Another embodiment of the present invention provides a crystalline form of Di-p-toluyl-D tartarate salt of zopiclone. The crystalline form of Di-p-toluyl-D tartarate salt of zopiclone can be characterized by having an X-ray diffraction (XRD) pattern substantially in accordance with FIG. 1.

Figure 2:
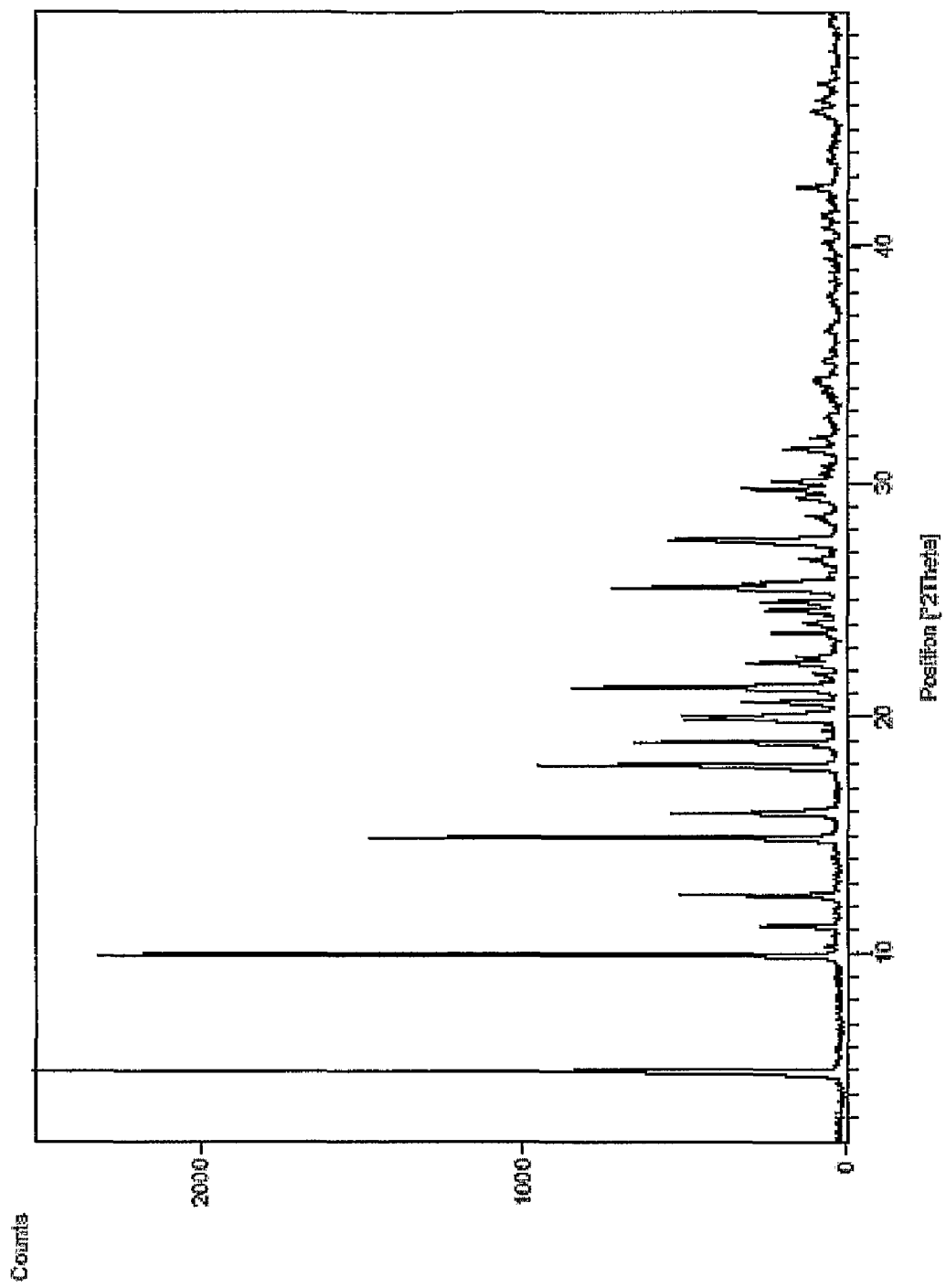
FIG. 2 is a characteristic X-ray powder diffraction pattern of a dextrorotatory isomer of zopiclone in crystalline form.

Another embodiment of the present invention provides a crystalline form of a dextrorotatory isomer of zopiclone. The crystalline form of a dextrorotatory isomer of zopiclone can be characterized by having an XRD pattern substantially in accordance with FIG. 2. The X-Ray powder diffractograms of FIGS. 1 and 2 were recorded at a PANalytical X'Pert PRO X-Ray Diffractometer.

Yet another embodiment of the present invention provides a process for the preparation of the dextrorotatory isomer of zopiclone. Generally, the process involves (a) providing a reaction mixture comprising zopiclone in one or more first solvents and one or more optically active acids; (b) crystallizing the desired isomer by substantially removing the first solvent and adding one or more second solvents; (c) recrystallizing a salt with a solvent selected from the group consisting of an ether-containing solvent, alcohol-containing solvent, ketone-containing solvent and mixtures thereof; (d) alkalizing the recrystallized salt with an inorganic base in water or a solvent mixture comprising water and a halogenated solvent to obtain the dextroisomer; and (e) isolating the resulting dextroisomer.

In step (a) of the process of the present invention, a reaction mixture is formed by mixing zopiclone in at least an optically active acid in one or more solvents. The optically active acid can be any of the aforedescribed optically active acids. Suitable solvents include, but are not limited to, ethers such as cyclic ethers, e.g., tetrahydrofuran, 4-dimethyl-tetrahydrofuran, oxetane, methyl-oxetane, dimethyl-oxetane, 3-methyl-tetrahydrofuran, 3-ethyl-tetrahydrofuran, oxepane, oxocane, oxonane, oxecane, perfluoroalkyl oxirane and the like; aliphatic ethers, e.g., isopropyl ether, methyl t-butyl ether and the like; alcohols such as $C_1$-$C_{12}$ alcohols, e.g., methanol, ethanol, butanol, tertiary butyl alcohol and the like; halogenated solvents such as dichloromethane, carbon tetrachloride, chloroform, and the like; and mixtures thereof.

In step (b) of the process of the present invention, the salt of zopiclone, e.g., a crystalline di-p-toluyl-D tartarate salt of zopiclone, is isolated by techniques known in the art, e.g., evaporating the solvent from the solution, crystallizing the salt and the like. For example, the salt can be isolated by evaporation and then subjected to one or more purification steps in a mixture of an alcohol and/or ether. Alternatively, the salt can be isolated by crystallizing the salt by such methods as cooling the solution at a temperature below reflux, and more preferably at a temperature of about 20 to about 25° C. The salt can be crystallized from a suitable solvent such as $C_1$-$C_{12}$ alcohols, e.g., methanol, ethanol and the like, ethers, e.g., isopropyl ether, and the like and mixtures thereof. Preferably, prior to crystallization, the cyclic ether is removed from the solution, e.g., by evaporating the cyclic ether from the solution or by distilling out the cyclic ether.

In step (c) of the process of the present invention, the crystallized salt such as a crystallized di-p-toluyl-D tartarate salt of zopiclone is recrystallized in a solvent selected from the group consisting of an ether-containing solvents, alcohol-containing solvents, ketone-containing solvents and mixtures thereof as described herein.

In step (d) of the process of the present invention, the recrystallized salt is alkalized in a base and in either water or a mixture of water and halogenated solvent to provide the dextrorotatory isomer of zopiclone. The base can be an organic or inorganic base. Suitable inorganic bases include, but are not limited to, hydroxides, carbonates, bicarbonates, alkoxides and oxides of alkali or alkaline earth metals. Useful alkali metal compounds include the lithium, sodium and potassium compounds with the sodium and potassium compounds being preferred. Useful alkaline earth metal compounds include the calcium and magnesium compounds with the magnesium compounds being preferred. Representative examples of such bases include sodium hydroxide, potassium hydroxide, magnesium hydroxide, magnesium oxide, sodium carbonate, potassium carbonate, sodium bicarbonate, potassium bicarbonate, sodium tert-butoxide and potassium tert-butoxide. The more preferred bases are hydroxides of sodium and potassium. Suitable organic base include amines such as primary, secondary or tertiary amines. The preferred organic amines are triethyl amine and N,N-diisopropylethylamine.

Suitable halogenated solvents include, but are not limited to, dichloromethane, carbon tetrachloride, chloroform, and the like and mixtures thereof.

In step (e) of the process of the present invention, the resulting dextroisomer is isolated by, for example, crystallization using a solvent such as an alcohol, ether and/or ketone as described herein.

By performing the processes of the present invention, substantially pure eszopiclone can be obtained. By "substantially pure" is meant a dextrorotatory isomer of zopiclone or a pharmaceutically acceptable salt thereof having a purity of greater than or equal to about 98%, preferably a purity of greater than or equal to about 99% and more preferably a purity of greater than or equal to about 99.5% as determined by high performance liquid chromatography (HPLC) using a Shimadzu LC 2010 A (manufactured by Shimadzu Corporation) column: Phenomenex Gemini, C18 (250X4.6, 5 Micron) and as compared to the crude product. Also, the content of levorotatory isomer present in the substantially pure dextrorotatory isomer of zopiclone or a pharmaceutically acceptable salt thereof as determined by HPLC can be at a level of less than about 0.50%, preferably less than about 0.25% and more preferably less than about 0.15%. In another embodiment, the substantially pure dextrorotatory isomer of zopiclone or a pharmaceutically acceptable salt thereof can be substantially free of any unknown impurity, e.g., a content of less than about 0.1% of impurities.

Another embodiment provides eszopiclone having an enantiomeric purity of greater than or equal to about 98%, preferably an enantiomeric purity of greater than or equal to about 99% and more preferably an enantiomeric purity of greater than or equal to about 99.5% as determined by HPLC using an Agilent 1100 Series column Chiralpak AS-H [250X4.6].

Another aspect of the present invention is directed to a pharmaceutical composition containing at least the substantially pure dextrorotatory isomer of zopiclone or a pharmaceutically acceptable salt thereof, e.g., crystalline Di-p-toluyl-D tartarate salt of zopiclone, of the present invention and at least one pharmaceutically acceptable excipient. Such pharmaceutical compositions may be administered to a mammalian patient in any dosage form, e.g., liquid, powder, elixir, injectable solution, etc. Dosage forms may be adapted for administration to the patient by oral, buccal, parenteral, ophthalmic, rectal and transdermal routes. Oral dosage forms include, but are not limited to, tablets, pills, capsules, troches, sachets, suspensions, powders, lozenges, elixirs and the like. The substantially pure dextrorotatory isomer of zopiclone or a pharmaceutically acceptable salt thereof of the present invention also may be administered as suppositories, ophthalmic ointments and suspensions, and parenteral suspensions, which are administered by other routes. The dosage forms may contain the substantially pure dextrorotatory isomer of zopiclone or a pharmaceutically acceptable salt thereof of the present invention as is or, alternatively, as part of a composition. The pharmaceutical compositions may further contain one or more pharmaceutically acceptable excipients as described herein.

The capsule dosages will contain the substantially pure dextrorotatory isomer of zopiclone or a pharmaceutically acceptable salt thereof of the present invention within a capsule which may be coated with gelatin. Tablets and powders may also be coated with an enteric coating. The enteric-coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients contemplated by the present invention include binders such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants such as magnesium stearate, calcium stearate and sodium stearyl fumarate; flavorings; sweeteners; preservatives; pharmaceutically acceptable dyes and glidants such as silicon dioxide.

Actual dosage levels of the substantially pure dextrorotatory isomer of zopiclone or a pharmaceutically acceptable salt thereof of the present invention in the compositions of the invention may be varied to obtain an amount of substantially pure dextrorotatory isomer of zopiclone or a pharmaceutically acceptable salt thereof that is effective to obtain a desired therapeutic response for a particular composition and method of administration. The selected dosage level therefore depends upon such factors as, for example, the desired therapeutic effect, the route of administration, the desired duration of treatment, and other factors. The total daily dose of the compounds of this invention administered to a host in single or divided dose and can vary widely depending upon a variety of factors including, for example, the body weight, general health, sex, diet, time and route of administration, rates of absorption and excretion, combination with other drugs, the severity of the particular condition being treated, etc.

In one embodiment, the substantially pure dextrorotatory isomer of zopiclone or a pharmaceutically acceptable salt thereof of the present invention for use in the pharmaceutical compositions of the present invention can have a $D_{50}$ and $D_{90}$ particle size of less than about 400 microns, preferably less than about 200 microns, more preferably less than about 150 microns, still more preferably less than about 50 microns and most preferably less than about 15 microns. The particle size can be determined by such techniques as, for example, Malvern light scattering, a laser light scattering technique, etc., using, e.g., a Malvern Mastersizer 2000 It is noted the notation $D_x$ means that X % of the particles have a diameter less than a specified diameter D. Thus, a $D_{50}$ of about 250 microns means that 50% of the particles in a substantially pure dextrorotatory isomer of zopiclone composition have a diameter less than about 250 microns. The particle sizes of the substantially pure dextrorotatory isomer of zopiclone or a pharmaceutically acceptable salt thereof can be obtained by, for example, any milling, grinding, micronizing or other particle size reduction method known in the art to bring the solid state substantially pure dextrorotatory isomer of zopiclone into any of the foregoing desired particle size range.

The following examples are provided to enable one skilled in the art to practice the invention and are merely illustrative of the invention. The examples should not be read as limiting the scope of the invention.

Example 1

Preparation of Dextroisomer of Di-p-toluyl-D-tartate Salt of Zopiclone

A solution of zopiclone (25 g, 0.064 mol) in tetrahydrofuran (1000 ml) was added to a solution of anhydrous (+) Di-p-toluyl-D-tartaric acid (25 g, 0.064 mol) in tetrahydrofuran (125 ml). The reaction mixture was stirred for 1 hour and concentrated under vacuum to obtain the crude salt. Ethanol (375 ml) was added to the crude salt, followed by evaporation of solvent to remove any traces of tetrahydrofuran. Ethanol (375 ml) was again added to precipitate the salt. The crude diastereomeric salt was purified in a mixture of ethyl alcohol and isopropyl ether (7:3) under reflux for 15 minutes and allowed to cool to at room temperature followed by filtration. The resulting salt was further recrystallised under the same conditions to obtain the pure salt.

Example 2

Preparation of Pure Dextroisomer of Di-p-toluyl-D-tartate Salt of Zopiclone

A solution of 300 g (+)Di-p-toluyl-D-tartaric acid in 1500 ml methanol was added to a suspension of 300 g zopiclone in 9000 ml methanol. Methanol was evaporated under vacuum distillation followed by addition of 4500 ml of methanol. The resulting crude salt was obtained by filtration.

Next, the pure dextroisomer of Di-p-toluyl-D-tartate salt of zopiclone was obtained by crystallizing the crude salt with 17000 ml of methanol and 13000 ml of isopropyl ether. The resulting pure salt was further recrystallised under the same conditions to obtain the pure salt.

Example 3

Preparation of Dextroisomer of Di-p-toluyl-D-tartate Salt of Zopiclone

Zopiclone (50 g) was added to a solution of 50 g (+)Di-p-toluyl-D-tartaric acid in 1000 ml of acetone followed by reflux for 2-3 hours. The salt was obtained by filtration at room temperature and had an enantiomeric purity of not less than 95% as measured by chiral HPLC.

Next, the pure dextroisomer of Di-p-toluyl-D-tartate salt of zopiclone was obtained by leaching the salt with 500 ml of methanol followed by filtration. The pure dextroisomer of Di-p-toluyl-D-tartate salt of zopiclone had an enantiomeric purity of not less than 97% as measured by chiral HPLC.

Example 4

Preparation of Dextroisomer of Di-p-toluyl-D-tartate Salt of Zopiclone

Zopiclone (50 g) was added to a solution of 50 g (+)Di-p-toluyl-D-tartaric acid in 400 ml of methanol followed by reflux for 5 hours. The crude salt was obtained by filtration at room temperature and had an enantiomeric purity of not less than 95% as measured by chiral HPLC.

Next, the pure dextroisomer of Di-p-toluyl-D-tartate salt of zopiclone was obtained by leaching the above salt with 500 ml of acetone followed by the filtration. The pure dextroisomer of Di-p-toluyl-D-tartate salt of zopiclone had an enantiomeric purity of not less than 97% as measured by chiral HPLC.

Example 5

Preparation of Dextroisomer of Zopiclone

The salt obtained in Example 1 was dissolved in water (160 ml) and dichloromethane (160 ml). The pH of the solution was adjusted to about 11 by slow addition of a 20% sodium hydroxide solution. The mixture was kept standing and the organic layer was allowed to separate. The aqueous layer was extracted twice with dichloromethane. Next, the combined organic phases were washed with water. This was followed by evaporation of the solvent and stripping with acetone and further purification in acetone (64 ml) to recover the dextrorotatory isomer (5.5 g) of zopiclone having an optical rotation of $[\alpha]_D^{20}$ is +135±3° (c=1%, acetone). The content of the levorotatory isomer was less than 0.15%.

Example 6

Preparation of Dextroisomer of Zopiclone

The salt obtained in Example 4 was suspended in 400 ml of water, basified with 20% NaOH solution and filtered to provide the pure dextroisomer of zopiclone. The dextroisomer of zopiclone had a purity of not less than 99%, as measured by HPLC, and an enantiomeric purity of not less than 99%, as measured by chiral HPLC.

Example 7

Preparation of Dextroisomer of Zopiclone

The salt obtained in Example 4 was suspended in 400 ml of water, basified with 20% NaOH solution and filtered to provide the dextroisomer of zopiclone. The dextroisomer of zopiclone had a purity of not less than 99%, as measured by HPLC, and an enantiomeric purity of not less than 99%, as measured by chiral HPLC.

Next, the dextroisomer of zopiclone was crystallized with 500 ml of acetone in the presence of 5 ml acetic anhydride followed by the filtration at 0-5° C. to provide 10 g of pure dextroisomer of zopiclone. The pure dextroisomer of zopiclone was free from metabolite impurities and had a purity of not less than 99.9%, as measured by HPLC, and an enantiomeric purity of not less than 99% with unwanted isomer not more than 1%.

Example 8

Particle Size of Dextroisomer of Zopiclone

The crystal particle size of the dextroisomer of zopiclone obtained from the above examples can be reduced by jet milling the particle size to less than 10 microns.

Example 9

Preparation of Amorphous Form of Dextroisomer of Zopiclone

Pure dextroisomer of zopiclone (5 g) is added to an alcoholic solvent such as methanol, ethanol, isopropyl alcohol or a combination thereof and then an anti-solvent such as hexane, heptane and toluene is added.

Example 10

Preparation of Amorphous Form of Dextroisomer of Zopiclone

Pure dextroisomer of zopiclone (5 g) is added to an alcoholic solvent with water.

Example 11

Preparation of Amorphous Form of Dextroisomer of Zopiclone

Pure dextroisomer of zopiclone (5 g) was added to water alone.

Example 12

Crystalline Form of Di-p-toluyl-D-tartarate Salt of Zopiclone

The dextroisomers of Di-p-toluyl-D-tartate salt of zopiclone of Examples 1-4 and the dextroisomers of zopiclone of Examples 5-7 were analyzed for their crystalline nature. The dextroisomers of Di-p-toluyl-D-tartate salt of zopiclone of Examples 1-4 were identified as having the characteristic X-ray powder diffraction pattern of FIG. 1. The dextroisomers of zopiclone of Examples 5-7 were identified as having the characteristic X-ray powder diffraction pattern of FIG. 2.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention.

A substantially pure dextrorotatory isomer of zopiclone or a pharmaceutically acceptable salt thereof and crystalline forms thereof are provided. Also provided are pharmaceutical compositions containing same.

SEQUENCE LISTING

Not applicable

What is claimed is:

1. A crystalline form of a dextrorotatory isomer of zopiclone, characterized as having an X-ray diffraction pattern in accordance with FIG. 2.

2. A pharmaceutical composition comprising a therapeutically effective amount of the crystalline form of the dextrorotatory isomer of zopiclone of claim 1 and at least one pharmaceutically acceptable carrier, diluent or excipient.

3. The pharmaceutical composition of claim 2, wherein the crystalline form of the dextrorotatory isomer of zopiclone is a micronized crystalline form of the dextrorotatory isomer of zopiclone having a particle size distribution equal to or less than about 200 microns.

4. The pharmaceutical composition of claim 2, wherein the crystalline form of the dextrorotatory isomer of zopiclone is a micronized crystalline form of the dextrorotatory isomer of zopiclone having a particle size distribution equal to or less than about 150 microns.

5. The pharmaceutical composition of claim 2, wherein the crystalline form of the dextrorotatory isomer of zopiclone is a micronized crystalline form of the dextrorotatory isomer of zopiclone having a particle size distribution equal to or less than about 50 microns.

6. The pharmaceutical composition of claim 2, wherein the crystalline form of the dextrorotatory isomer of zopiclone is a micronized crystalline form of the dextrorotatory isomer of zopiclone having a particle size distribution equal to or less than about 15 microns.

7. The pharmaceutical composition of claim 2, which is in a solid form.

8. The pharmaceutical composition of claim 2, which is a tablet or capsule.

* * * * *